United States Patent
Kwon et al.

(10) Patent No.: US 11,123,268 B2
(45) Date of Patent: Sep. 21, 2021

(54) TABLET FORM OF COSMETIC COMPOSITION OBTAINED BY DIRECT TABLETING WITHOUT MOLDING PLATE AND METHOD FOR PREPARING SAME

(71) Applicant: COSMAX, INC., Gyeonggi-do (KR)

(72) Inventors: Sung Ho Kwon, Seoul (KR); Sung Yong Kim, Gyeonggi-do (KR); Eun Ju Seo, Gyeonggi-do (KR); Myeong Sam Park, Seoul (KR)

(73) Assignee: COSMAX, INC., Gyeonggi-do (KR)

( * ) Notice: Subject to any disclaimer, the term of this patent is extended or adjusted under 35 U.S.C. 154(b) by 195 days.

(21) Appl. No.: 16/084,487

(22) PCT Filed: Feb. 24, 2017

(86) PCT No.: PCT/KR2017/002060
§ 371 (c)(1),
(2) Date: Sep. 12, 2018

(87) PCT Pub. No.: WO2017/160008
PCT Pub. Date: Sep. 21, 2017

(65) Prior Publication Data
US 2020/0163845 A1 May 28, 2020

(30) Foreign Application Priority Data
Mar. 16, 2016 (KR) .................. 10-2016-0031357

(51) Int. Cl.
*A61K 8/25* (2006.01)
*A61K 8/27* (2006.01)
(Continued)

(52) U.S. Cl.
CPC .............. *A61K 8/0225* (2013.01); *A61K 8/25* (2013.01); *A61K 8/27* (2013.01); *A61K 8/29* (2013.01);
(Continued)

(58) Field of Classification Search
CPC .......... A61K 8/0225; A61K 8/25; A61K 8/27; A61K 8/29; A61K 8/34; A61K 8/731;
(Continued)

(56) References Cited

U.S. PATENT DOCUMENTS 5,063,050 A * 11/1991 Verdon ............... A61K 8/0216
424/401
2007/0196528 A1 * 8/2007 Bonnet ................. A61Q 19/00
424/778
(Continued)

FOREIGN PATENT DOCUMENTS

JP 2007-055941 A 3/2007
JP 2015-024962 A 2/2015
(Continued)

OTHER PUBLICATIONS

Dictionary.Com, definition of Spray as a verb, 2020, from https://www.dictionary.com/browse/spray?s=t (Year: 2020).*
(Continued)

*Primary Examiner* — Melissa L Fisher
*Assistant Examiner* — Ayaan A Alam
(74) *Attorney, Agent, or Firm* — Harness, Dickey & Pierce, P.L.C.

(57) ABSTRACT

The present disclosure relates to a tablet-form cosmetic composition obtained by mixing a powder blend containing makeup powder and a viscosity modifier with an aqueous dispersion containing water, an alcohol, a polymer for lubricant and a polysaccharide for binder, granulating the resultant mixture, and shaping the resultant granules with a tablet press, and a method for preparing the same. According to the present disclosure, there is provided a tablet-form cosmetic composition obtained by direct tablet pressing without using a shaping pan. The tablet-form cosmetic composition shows significantly improved aesthetic beauty
(Continued)

and portability, while maintaining a cosmetic effect of the conventional powder- or cake-type powder cosmetic composition. In addition, the tablet-form cosmetic composition is shaped through granulation, and thus solves the problem of air-filling in the tablets upon pressing, shows a larger diameter as compared to the similar conventional particulate powder cosmetic composition, and allows various designs.

7 Claims, 3 Drawing Sheets

(51) Int. Cl.
    *A61K 8/29*     (2006.01)
    *A61K 8/34*     (2006.01)
    *A61K 8/73*     (2006.01)
    *A61K 8/92*     (2006.01)
    *A61K 8/02*     (2006.01)

(52) U.S. Cl.
    CPC .............. *A61K 8/34* (2013.01); *A61K 8/731* (2013.01); *A61K 8/92* (2013.01); *A61K 2800/624* (2013.01); *A61K 2800/805* (2013.01)

(58) Field of Classification Search
    CPC ................ A61K 8/92; A61K 800/624; A61K 800/805
    See application file for complete search history.

(56) References Cited

U.S. PATENT DOCUMENTS

2011/0180445 A1    7/2011  Hurwitz
2015/0359713 A1*  12/2015  Fassih ................ A61K 8/11
                                          424/401

FOREIGN PATENT DOCUMENTS

| KR | 10-2003-0077193 A | 10/2003 |
| KR | 10-1194460 B1 | 10/2012 |
| KR | 10-2015-0021372 A | 3/2015 |

OTHER PUBLICATIONS

International Search Report, dated Jun. 30, 2017 issued in International Application No. PCT/KR2017/002060, with English Translation.

* cited by examiner

TABLET FORM OF COSMETIC COMPOSITION OBTAINED BY DIRECT TABLETING WITHOUT MOLDING PLATE AND METHOD FOR PREPARING SAME

CROSS-REFERENCE TO RELATED APPLICATIONS

This application is a national phase application of PCT Application No. PCT/KR2017/002060, filed on 24 Feb. 2017, which claims benefit of Korean Patent Application KR 10-2016-0031357, filed on 16 Mar. 2016. The entire disclosure of the application identified in this paragraph is incorporated herein by reference.

TECHNICAL FIELD

The present disclosure relates to a tablet-type cosmetic composition obtained through direct tablet pressing by eliminating a shaping pan included in conventional powder-type or cake-type cosmetics, and a method for preparing the same. More particularly, the present disclosure relates to a tablet-form cosmetic composition obtained by mixing a powder blend containing makeup powder and a viscosity modifier with an aqueous dispersion containing water, an alcohol, a polymer for lubricant and a polysaccharide for binder, granulating the resultant mixture, and shaping the resultant granules with a tablet press, and a method for preparing the same.

BACKGROUND

In general, a powder-type cosmetic composition includes a dry powder pigment, such as an inorganic pigment, organic pigment or an extender pigment, and a liquid binder, such as natural oil, silicon oil or a moisturizer. Thus, such a powder-type cosmetic composition causes severe dust flying and requires a shaping pan or frame during its shaping.

A particulate cosmetic composition has some advantages, including a design differentiated from that of a conventional powder-type cosmetic composition or a powder cosmetic composition pressed in a pan (shaping pan or frame), high portability and relatively low dust flying.

The particulate cosmetic compositions according to the related art was obtained by a method which includes agglomerating and rounding particles to form pill shapes, or a method for preparing microparticles through tablet pressing. For example, "Microparticulate Powder Makeup Cosmetic Agent and Method for Preparing the same" (Korean Patent Publication No. 10-1194460) is known as the method for preparing microparticles.

However, such a pill-shaped cosmetic composition has limitations in that it requires a long production time, and does not allow various designs but merely allows a round design. In addition, the method for preparing microparticles through tablet pressing has limitations in that it essentially uses zinc stearate and bentonite and merely allows a limited design and production of microparticles having a diameter of 5 mm or less.

Under these circumstances, the present inventors have conducted many studies to overcome the above-mentioned problems according to the related art. As a result, it has been found that a tablet-form cosmetic composition not disclosed in the field of cosmetics for skin application but disclosed in the field of pharmaceuticals for oral administration or food could be obtained by using a direct tablet pressing without using a pan (shaping pan or frame). The present disclosure is based on this finding. Particularly, the present inventors have recognized that powder used for makeup cosmetic agents is amorphous and has many voids to show a large angle of repose, thereby making it difficult to provide larger tablet shapes with various designs. To overcome this, a powder granulation step was introduced before a tablet pressing step to provide a small angle of repose and to allow the internal air to be discharged with ease by the tablet pressing pressure. Thus, it was possible to form a tablet-type cosmetic composition having a larger size like the commercially available tablets and including various designs.

SUMMARY

Technical Problem

A technical problem to be solved by the present disclosure is to overcome the above-mentioned limitations according to the related art and to provide a tablet-form makeup cosmetic composition having a relatively large diameter and various designs, and a method for preparing the same.

As used herein, the term 'shaping pan' means a pan for receiving and shaping the conventional powder-type or cake-type cosmetic agent, and the term 'tablet' means a solid formulation used generally in the field of pharmaceuticals and having a size of 5 mm or more, and can be differentiated from powder, microparticles or granules having a smaller size.

Technical Solution

In one general aspect, there is provided a method for preparing a tablet-form makeup cosmetic composition, which includes the steps of:

(a) mixing makeup powder with a viscosity modifier to provide a powder blend;

(b) forming a granular cosmetic composition, while spraying an aqueous dispersion containing water, an alcohol, a polymer for lubricant and a polysaccharide for binder to the powder blend;

(c) drying the granular cosmetic composition; and (d) carrying out direct tablet pressing of the dried granular cosmetic composition without using a shaping pan to obtain a tablet-form makeup cosmetic composition.

In the method for preparing a tablet-form makeup cosmetic composition according to the present disclosure, the makeup powder in (a) may be any type of powder used conventionally for a makeup cosmetic agent. Preferably, the makeup powder may be at least one makeup powder selected from the group consisting of talc, mica, synthetic mica, sericite, silica, titanium dioxide, silicon powder, boron powder, zinc oxide, nylon powder, polymethacrylate powder, urethane powder, acrylate (co)polymer, polyethylene (co)polymer, organic pigments, inorganic pigments and nacreous pigments.

In the method for preparing a tablet-form makeup cosmetic composition according to the present disclosure, the viscosity modifier in (a) may be any type of viscosity modifier which is used conventionally for a cosmetic composition, functions to increase the viscosity of the content, and serves as a binder in a powder product. Preferably, the viscosity modifier may be a water soluble powdery viscosity modifier including at least one water soluble thickening agent selected from the group consisting of carrageenan, agar, gellan gum, xanthane gum, cellulose gum and starch;

and/or at least one inorganic gelling agent selected from the group consisting of montmorillonite, hectorite, silicate, kolin and zeolite.

In the method for preparing a tablet-form makeup cosmetic composition according to the present disclosure, the powder blend in (a) may optionally further include at least one oil phase selected from the group consisting of silicone oil, hydrocarbon oil, wax, natural oil and animal/vegetable liquid oil and fat. The oil generally functions to agglomerate powder and to impart a feeling of use, adhesion and persistency in a powder product. According to an embodiment, the oil functions to enhance a feeling of use by imparting a feeling of use, adhesion and persistency. Such oil may not be incorporated to the composition according to the present disclosure, but may be incorporated to the composition in an amount of 1-5 wt %, preferably. When the oil is used excessively in an amount larger than 5 wt %, surface caking may occur to cause degradation of applicability.

In the method for preparing a tablet-form makeup cosmetic composition according to the present disclosure, the lubricant in (b) generally functions to prevent adhesion of the content in a tablet to a mold and to transfer pressure adequately. Any type of polymer used conventionally for a makeup cosmetic agent may be used, as long as it has functions as a lubricant. Preferably, the lubricant may be a polymer functioning as a lubricant and selected from the group consisting of glycerin, sorbitol, mannitol, xylitol, glycols and polyhydric alcohols.

In the method for preparing a tablet-form makeup cosmetic composition according to the present disclosure, the polysaccharide for binder in (b) may be any type of polysaccharide which functions to increase the binding force in the content and to impart stability as a binder, serves to retain the shape, and has the functions as a binder used conventionally for a makeup cosmetic agent. Preferably, the polysaccharide may be selected from the group consisting of cellulose, trehalose and glucose.

In the method for preparing a tablet-form makeup cosmetic composition according to the present disclosure, the powder blend in (a) has a content of 65-90 wt % and the aqueous dispersion in (b) has a content of 10-35 wt %. When each of the powder blend and the aqueous dispersion has the above-defined content, it is possible to facilitate granulation and shaping of tablets. As used herein, 'content on wt % basis' means the content based on the total weight of the composition before the drying step in the preparation process.

In the method for preparing a tablet-form makeup cosmetic composition according to the present disclosure, water and alcohol in the aqueous dispersion in (b) are essential ingredients for granulating the cosmetic composition according to the present disclosure and may be used in an amount of 2-34.94 wt %, preferably in an amount of 15-25 wt %, based on the total weight of the composition. When water and alcohol are used in an excessively small amount, it is not possible to carry out granulation sufficiently, thereby making it difficult to form tablets having a large diameter.

In another aspect, there is provided a tablet-form makeup cosmetic composition obtained by mixing the following ingredients and carrying out direct tablet pressing without any shaping pan:

(a) 65-90 wt % of a powder blend containing makeup powder and a viscosity modifier; and (b) 10-35 wt % of aqueous dispersion containing water, an alcohol, a polymer for lubricant and a polysaccharide for binder.

According to an embodiment of the present disclosure, there is provided a tablet-form makeup cosmetic composition obtained by the above-described method according to the present disclosure. The present inventors were able to provide a tablet-form makeup cosmetic composition for the first time according to the above-described method.

In the tablet-form makeup cosmetic composition according to the present disclosure, the tablet has a diameter of 5 mm or more, preferably 10 mm or more, and more preferably 10-30 mm, while showing shaping stability. The present inventors have recognized that powder used for a makeup cosmetic agent is amorphous, has a lot of voids and has a large angle of repose, thereby making it difficult to form tablets having a large diameter and various designs. To overcome this, a powder granulation step was introduced before a tablet pressing step to reduce the angle of repose and to allow for the internal air to be discharged with ease by tablet pressing pressure. In this manner, it was possible to provide a tablet-form cosmetic composition having a larger diameter and various designs.

In the tablet-form makeup cosmetic composition according to the present disclosure, the tablet may be pressed by various types of molds, including not only a general oval shape but also into various shapes, such as a circular, heart-like or flower-like shape, and thus may be formed into various shapes. According to an embodiment of the present disclosure, not only oval tablets having a size of 10-30 mm but also flower-shaped tablets having a size of about 20 mm are pressed, and the tablets are shown to have shaping stability. In addition, the makeup cosmetic composition according to the present disclosure may be mixed with powder having various colors and pressed into tablets so that one tablet may show multiple colors.

BEST MODE FOR CARRYING OUT INVENTION

Hereinafter, the present disclosure will be explained in more detail.

The tablet-form makeup cosmetic composition according to the present disclosure includes 65-90 wt % of a powder blend containing makeup powder and a water soluble powdery viscosity modifier, and 10-35 wt % of an aqueous dispersion containing water, an alcohol, a polymer having a function as a lubricant and a polysaccharide having a function as a binder. More preferably, the composition according to the present disclosure includes 70-85 wt % of the powder blend and 15-30 wt % of the aqueous dispersion.

Referring to the powder blend and the aqueous dispersion, the powder blend is obtained through a dispersion step and a mixing step, like the conventional powder products. Next, while the aqueous dispersion is sprayed to the powder blend, granular content is formed from the powder blend and the aqueous dispersion by using a granulation device. Then, the granular content is dried partially or completely to provide a finished content, which, in turn, is subjected to direct tablet pressing in the absence of a pan (shaping pan or frame) to provide tablets. Finally, the particles are dried. Herein, when the granular content is dried completely to provide the finished content, the final drying step is not required.

Particularly, the powder blend may include 0.1-20 wt % of the water soluble powdery viscosity modifier, 40-89.9 wt % of a powder phase and 0-5 wt % of an oil phase.

Particularly, the aqueous dispersion may include 2-34.94 wt % of a mixture of water with alcohols, 0.01-3 wt % of the polymer having a function as a lubricant, and 0.05-5 wt % of the polysaccharide having a function as a binder. The mixture of water with an alcohol is used preferably in an amount of 15-25 wt %, and the mixing ratio of water and alcohol varies with the types of the polymer and polysaccharides or shapes of the granules. More preferably, alcohols may be used in an amount of 70-90 wt %.

According to an embodiment of the present disclosure, two main groups and three sub-groups for each main group were tested according to the compositions as shown in the following Table 1 (main ingredients and contents).

According to the following examples, 65-90 wt % (preferably 70-85 wt %) of the powder blend and 10-35 wt % (preferably 15-30 wt %) of the aqueous dispersion may be used. The powder blend of Group 1 includes 40-89.9 wt % of the powder phase, 0.1-20 wt % of the water soluble powdery viscosity modifier and 0-5 wt % of the oil phase, while the aqueous dispersion of Group 2 includes 2-34.94 wt % of the mixture of water with an alcohol, 0.01-3 wt % of the polymer and 0.05-5 wt % of the polysaccharide.

TABLE 1

| Main Groups | | Sub-Groups | | Content (wt %) |
|---|---|---|---|---|
| Group 1 | Powder blend | Group 1-1 | Powder phase | 40-89.9 |
| | | Group 1-2 | Water soluble powdery viscosity modifier | 0.1-20 |
| | | Group 1-3 | Oil phase | 0-5 |
| Group 2 | Aqueous dispersion | Group 2-1 | Mixture of water with an alcohol | 2-34.94 |
| | | Group 2-2 | Polymer for lubricant | 0.01-3 |
| | | Group 2-3 | Polysaccharide for binder | 0.05-5 |

The methods for preparing a tablet-form makeup cosmetic composition according to the present disclosure include the following steps: dispersing and mixing Group 1-1 to Group 1-3 of Group 1, or dispersing and mixing Group 2-1 to Group 2-3 of Group 2; forming granular content, while spraying Group 2 to Group 1; drying the granular content partially or completely to provide a finished content; carrying out direct tablet pressing of the content in the absence of a pan (shaping pan or frame) to form particles; and finally drying the tablets. However, when the granular content is dried completely to provide a finished content, the final drying step is not required.

Group 1-1 (powder phase) includes at least one powder selected from talc, mica, synthetic mica, sericite, silica, titanium dioxide, silicon powder, boron powder, zinc oxide, nylon powder, polymethacrylate powder, urethane powder, acrylate (co)polymer, polyethylene (co)polymer, organic pigments, inorganic pigments and nacreous pigments, wherein the powder may not be surface-treated or may be surface-treated with silicon, a metal salt, fatty acid, amino acid, lauroyl lysine, lecithin, or the like.

Group 1-2 (water soluble powdery viscosity modifier) includes at least one water soluble thickening agent, such as carrageenan, agar, gellan gum, xanthane gum, cellulose gum or starch, or a composite thereof; and at least one water soluble inorganic gelling agent, such as montmorillonite, hectorite, silicate, kaolin or zeolite.

Group 1-3 (oil phase) may include an ester selected from triethylhexanoin, diisostearyl palmitate and triglycerides; a silicon compound selected from dimethicone and phenyltrimethicone; a hydrocarbon selected from liquid paraffin, squalane, mineral oil and triglycerin; wax selected from castor ax, carnauba wax and jojoba wax; natural oil selected from olive oil, macadamia nut oil and sunflower oil; or oil selected from coconut oil, palm oil, hempseed oil and animal/vegetable liquid oil and fats; or a mixture thereof.

Group 2-1 (mixture of water with an alcohol) is a volatile alcohol mixed with water, wherein the volatile alcohol is a monohydric alcohol which may include methyl alcohol, propyl alcohol or ethyl alcohol, and the mixing ratio of water and the volatile alcohol may depend on the types of the polymer and polysaccharide and the shape of granules. More preferably, the alcohol may be used in an amount of 70-80 wt %.

Group 2-2 (polymer for lubricant) includes at least one polyhydric alcohol (alcohol having multiple hydroxyl groups per molecule) capable of being dissolved in water or an alcohol, and particular examples of such polyhydric alcohols include glycerin, sorbitol, mannitol, xylitol, glycols (butylene glycol, propylene glycol, diethylene glycol, dipropylene glycol, polyethylene glycol, etc.)

Group 2-3 (polysaccharide for binder) includes at least one polysaccharide capable of being dissolved in water or an alcohol, and particular examples thereof include cellulose, trehalose, glucose, etc.

Besides the above main ingredients, the composition may include, as additives not included in the above-mentioned Groups, a preservative, a concept ingredient, a trace amount of functional material, fragrance, dispersing agent, or the like.

The powder cosmetic composition may be applied to a powder-type product, including pact, blusher and eye shadow, and may have a variable composition depending on a desired color, pearl-like feeling or feeling of use.

Advantageous Effects

According to the embodiments of the present disclosure, there is provided a tablet-form cosmetic composition obtained by direct tablet pressing without using a shaping pan. The tablet-form cosmetic composition shows significantly improved aesthetic beauty and portability, while maintaining a cosmetic effect of the conventional powder- or cake-type powder cosmetic composition. In addition, the tablet-form cosmetic composition is shaped through granulation, and thus solves the problem of air-filling in the tablets upon pressing, shows a larger diameter as compared to the similar conventional particulate powder cosmetic agent, and allows various designs.

DETAILED DESCRIPTION

Exemplary embodiments now will be described more fully hereinafter. This disclosure may, however, be embodied in many different forms and should not be construed as limited to the exemplary embodiments set forth therein.

Examples 1-5 and Comparative Examples 1-5: Preparation of Cosmetic Compositions Each of the cosmetic compositions of Examples 1-5 and Comparative Examples 1-5 was prepared according to the composition (cosmetic composition) as shown in the following Table 2 (unit: wt %). Comparative Example 1 is a cosmetic composition containing no viscosity modifier (Group 1-2) which is an essential ingredient according to the present disclosure. Comparative Example 2 is a cosmetic composition having a content of oil phase larger than 5 wt %, wherein the oil phase is an optional ingredient according to the present disclosure. Comparative Example 3 is a cosmetic composition containing no polymer for lubricant (Group 2-2) which is an essential ingredient according to the present disclosure. Comparative Example 4 is a cosmetic composition containing no polysaccharide for binder (Group 2-3) which is an essential ingredient according to the present disclosure. Comparative Example 5 is a cosmetic composition containing no water and ethanol (Group 2-1) which are essential ingredients according to the present disclosure.

Particularly, in Group 1-2, xanthane gum, cellulose gum and starch were used as water soluble thickening agents, and hectorite and silicate were used as inorganic gelling agents. In addition, silicon oil such as dimethicone and phenyltrimethicone, ester oil such as triethylhexanoin and diisostearyl palmitate and a small amount of the other types of oil were used as oil.

Each of the compositions according to Examples 1-5 and Comparative Examples 1-5 was prepared by the method as described hereinafter.

1) Group 1-1 to Group 1-3 were dispersed and mixed by using a Henschel mixer, atomizer or jet mill to form a powder blend. However, in Comparative Example 5, Group 2-2 and Group 2-3 were mixed totally to form a powder blend.

2) Group 2-1 to Group 2-3 were dispersed and mixed by using an agi-mixer, homo-mixer and disper-mixer to form an aqueous dispersion. However, Comparative Example 5 was obtained without using this step.

3) While the aqueous dispersion of 2) was applied to the powder blend of 1), granular content was prepared by using a granulation device, and then was dried partially or completely. However, Comparative Example 5 was obtained without using this granulation step.

4) The content obtained from 3) was subjected to direct tablet pressing by using a tablet press in the absence of a pan (shaping pan or frame) to provide tables, and then a drying step was carried out. However, when the drying step was carried out completely in 3), the final drying step was not carried out.

Figure 1:
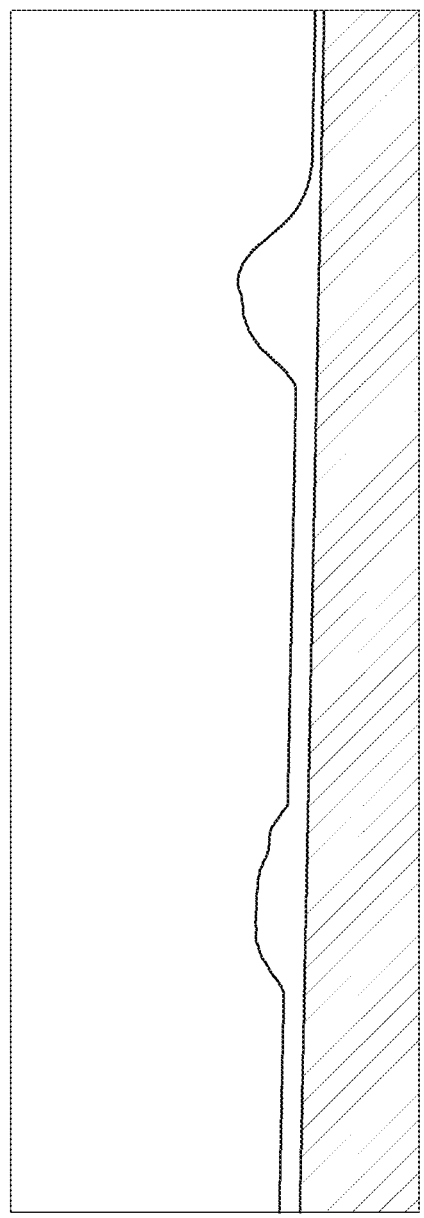
FIG. 1 is a photograph illustrating the angle of repose of the powder (Example 2) subjected to a granulation step as compared to the powder (Comparative Example 5) not subjected to a granulation step, wherein the granular powder is shown at the lower side and the non-granular powder is shown at the upper side.
Figure 2:
FIG. 2 is a photograph illustrating the shaping stability of the powder (Example 2) subjected to a granulation step, after it is pressed into tablets with a flower-like three-dimensional design, as compared to the powder (Comparative Example 5) not subjected to a granulation step, wherein the granular powder is shown at the lower side and the non-granular powder is shown at the upper side.
Figure 3:
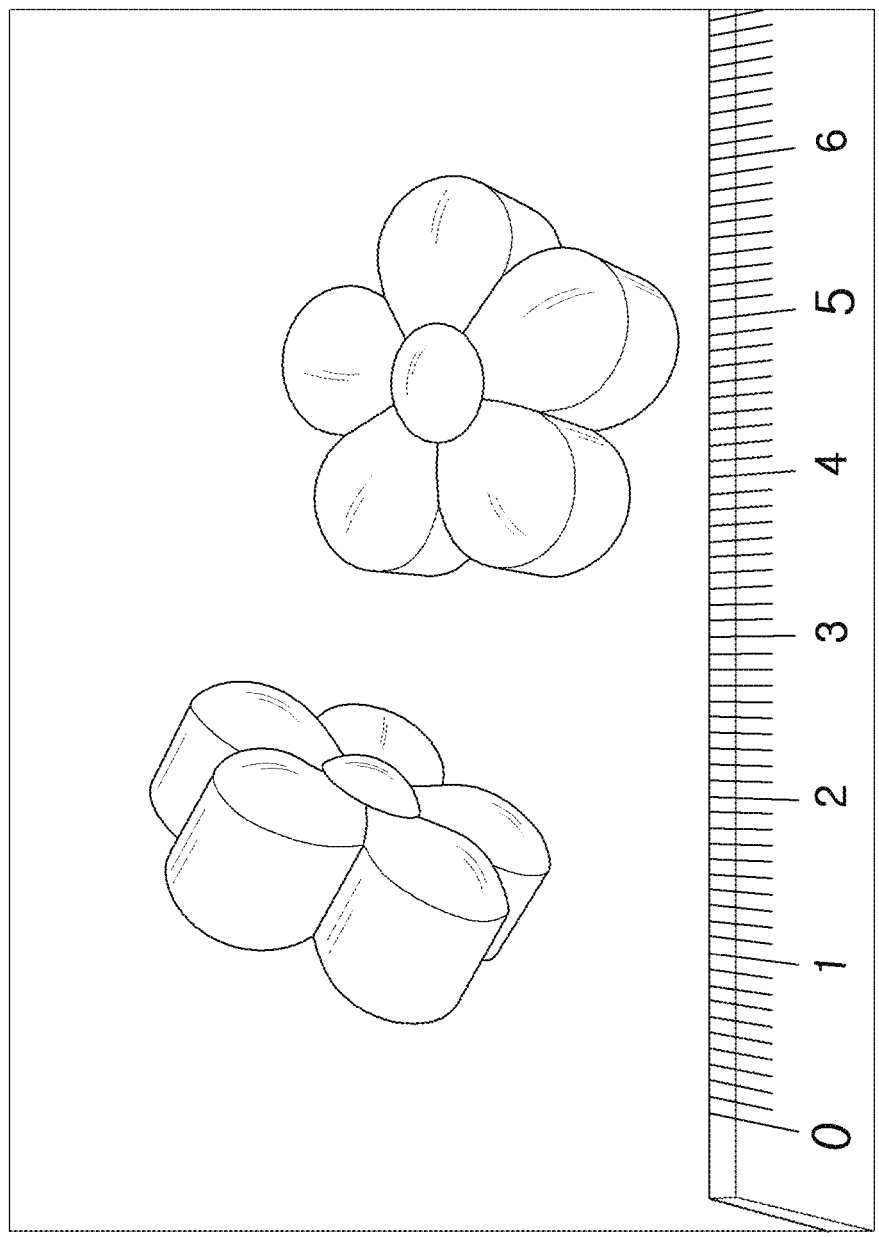
FIG. 3 is a photograph illustrating the powder (Example 2) subjected to a granulation step, after it is pressed into tablets with a flower-like three-dimensional design, wherein the powder has a diameter of 25 mm as determined by the scale provided at the bottom.

Before the tablet pressing in 4), the powder subjected to the granulation step (Example 2) and the powder not subjected to the granulation step (Comparative Example 5) were accumulated individually, and each type of powder was determined for its angle of repose. As shown in FIG. 1, it can be seen that the powder subjected to the granulation step has

TABLE 2

| | Ingredients | Example 1 | Example 2 | Example 3 | Example 4 | Com. Ex. 1 | Com. Ex. 2 | Com. Ex. 3 | Com. Ex. 4 | Com. Ex. 5 | Example 5 |
|---|---|---|---|---|---|---|---|---|---|---|---|
| Group 1-1 | talc | To 100 | To 100 | To 100 | To 100 | To 100 | To 100 | To 100 | To 100 | To 100 | To 100 |
| Group 1-1 | mica | 15.0 | 15.0 | 15.0 | 15.0 | 15.0 | 15.0 | 15.0 | 15.0 | 15.0 | — |
| | boron powder | 10.0 | 10.0 | 10.0 | 10.0 | 10.0 | 10.0 | 10.0 | 10.0 | 10.0 | 10.0 |
| | calcium carbonate | 10.0 | 10.0 | 10.0 | 10.0 | 10.0 | 10.0 | 10.0 | 10.0 | 10.0 | 10.0 |
| | nylon powder | 2.5 | 2.5 | 2.5 | 2.5 | 2.5 | 2.5 | 2.5 | 2.5 | 2.5 | 4.0 |
| | polyethylene powder | 2.0 | 2.0 | 2.0 | 2.0 | 2.0 | 2.0 | 2.0 | 2.0 | 2.0 | 2.5 |
| | metallic soap | 0.5 | 0.5 | 0.5 | 0.5 | 0.5 | 0.5 | 0.5 | 0.5 | 0.5 | 1.0 |
| | titanium dioxide | 10.0 | 10.0 | 10.0 | 10.0 | 10.0 | 10.0 | 10.0 | 10.0 | 10.0 | 5.0 |
| | zinc oxide | — | — | — | — | — | — | — | — | 2.0 | — |
| | coloring pigment | 3.5 | 3.5 | 3.5 | 3.5 | 3.5 | 3.5 | 3.5. | 3.5 | 3.5 | 3.5 |
| | nacreous pigment | — | — | — | — | — | — | — | — | — | 20 |
| Group 1-2 | water soluble thickening agent | 6.0 | 5.0 | — | 10.0 | — | 5.0 | 5.0 | 5.0 | 5.0 | 8.0 |
| Group 1-2 | inorganic gelling agent | 0.6 | 0.5 | 0.8 | — | — | 0.5 | 0.5 | 0.5 | 0.5 | 0.8 |
| Group 1-3 | oil phase | — | 2.0 | 2.0 | 2.0 | 2.0 | 5.5 | 2.0 | 2.0 | 2.0 | 5.0 |
| Group 2-1 | ethanol | 14.5 | 14.0 | 14.0 | 14.0 | 14.0 | 14.0 | 14.0 | 14.0 | — | 16 |
| Group 2-1 | purified water | 4.0 | 4.5 | 4.5 | 4.5 | 4.5 | 4.5 | 4.5 | 4.5 | — | 4.5 |
| Group 2-2 | Polymer for lubricant | 0.8 | 0.6 | 0.6 | 0.6 | 0.6 | 0.6 | — | 1.5 | 0.6 | 1.0 |
| Group 2-3 | Polysaccharide for binder | 0.9 | 0.9 | 0.9 | 0.9 | 0.9 | 0.9 | 1.5 | — | 0.9 | 1.5 | a smaller angle of repose as compared to the powder not subjected to the granulation step, and thus shows a relatively small amount of voids in the powder.

Test Example 1: Evaluation for Shaping Characteristics (Shaping Stability, Design Shaping Ability, Surface Caking)

Each of the cosmetic compositions according to Examples 1-4 and Comparative Examples 1-5 was evaluated for the shaping characteristics. The evaluation items include shaping stability, design shaping ability and surface caking. The shaping ability was evaluated by measuring the number of dropping at which point the tablets were broken by 50% or more, when they were pressed into a size of 10 mm, 20 mm or 30 mm and dropped onto a 3 mm rubber plate from a height of 30 cm. Herein, the evaluation criteria are as follows: less than 3=very unstable; 3 or more and less than 5=unstable; 5 or more and less than 10=stable; and 10 or more=very stable. The design shaping ability was evaluated by measuring the number of dropping at which point the tablets were broken by 50% or more, when they were pressed into a flower-like shape with a diameter of 20 mm and dropped onto a 3 mm rubber plate from a height of 30 cm. Herein, the evaluation criteria are as follows: less than 3=very unstable; 3 or more and less than 5=unstable; 5 or more and less than 7=stable; and 7 or more very stable. The surface caking was evaluated by determining whether the tablets cause a greasy caking phenomenon without smooth surface application (=yes) or not (=no). However, when the samples have no value as particles or compositions (e.g. when the particles are broken right after the shaping or are not formed at all, or are not suitable for evaluation due to the shape of particles), the evaluation results are marked as 'unstable'.

caking phenomenon, and thus has little or no value as cosmetic agents. In addition, Comparative Examples 1, 4 and 5 provide poor particle shaping ability and design shaping ability, even though they cause no surface caking phenomenon. Thus, it can be seen that the granulation process is effective for providing particle shaping ability and there is a need for using Group 1-2, Group 2-2 and Group 2-3 in an adequate range.

Test Example 2: Evaluation of Applicability (Caking-Free, Spreadability, Adhesion, Color Realization and Dust Flying-Free Characteristics)

Each of the cosmetic compositions according to Examples 1-5 and Comparative Examples 1-5 was evaluated for its applicability. Evaluation of the tablets obtained through tablet pressing of particles with a size of 20 mm were carried out, after they were used by 20 panels aged 25-40 on a scale of 10 points. The applicability test items include caking-free, spreadability, adhesion, color realization, dust flying-free and pay-off level characteristics.

TABLE 4

|  | Example 1 | Example 2 | Example 3 | Example 4 | Com. Ex. 1 | Com. Ex. 2 | Com. Ex. 3 | Com. Ex. 4 | Com. Ex. 5 | Example 5 |
|---|---|---|---|---|---|---|---|---|---|---|
| Caking-free | 5.0 | 4.9 | 5.0 | 4.9 | 4.9 | 0.2 | 0.8 | 4.7 | 1.5 | 4.9 |
| Spreadability | 4.2 | 4.0 | 4.1 | 3.9 | 3.6 | 1.0 | 2.3 | 3.7 | 3.4 | 4.1 |
| Adhesion | 4.0 | 4.2 | 3.9 | 4.1 | 1.2 | 4.0 | 1.2 | 1.3 | 1.5 | 3.5 |
| Color realization | 3.4 | 3.8 | 3.9 | 3.8 | 2.4 | 1.0 | 2.2 | 2.3 | 2.8 | 3.3 |
| Dust flying-free | 3.5 | 4.0 | 3.8 | 4.0 | 1.0 | 4.5 | 1.1 | 1.0 | 1.2 | 3.5 |
| Pay-off level | 4.5 | 4.6 | 4.4 | 4.5 | 1.5 | 0.8 | 1.0 | 1.5 | 1.5 | 4.2 |

* 5: very good, 4: good, 3: normal, 4: bad, 5: very bad

As can be seen from Table 4 (evaluation of applicability of Examples 1-5 and Comparative Examples 1-5), Comparative Example 1 provides poor results in terms of adhesion, color realization, dust flying-free and pay-off level characteristics; Comparative Example 2 provides poor results in terms of caking-free, spreadability, color realization and pay-off level characteristics; Comparative Examples 3 provides poor results in all terms; Comparative Example 4 provides poor results in terms of adhesion, color realization and dust flying-free characteristics; and Comparative Example 5 provides poor results in terms of caking-free, adhesion, dust flying-free and pay-off level characteristics. This results from the use of a specific ingredient in an excessive amount or the absence of a specific ingredient.

TABLE 3

|  |  | Example 1 | Example 2 | Example 3 | Example 4 | Com. Ex. 1 | Com. Ex. 2 | Com. Ex. 3 | Com. Ex. 4 | Com. Ex. 5 | Example 5 |
|---|---|---|---|---|---|---|---|---|---|---|---|
| Shaping Stability | 10 mm | very stable | very stable | very stable | very stable | unstable | very stable | very unstable | unstable | unstable | very stable |
| Shaping Stability | 20 mm | stable | very stable | stable | stable | very unstable | very stable | very unstable | very unstable | very unstable | very stable |
| Shaping Stability | 30 mm | stable | stable | stable | stable | very unstable | stable | very unstable | very unstable | very unstable | stable |
| Design Shaping Ability |  | stable | very stable | stable | stable | very unstable | stable | very unstable | very unstable | very unstable | stable |
| Surface Caking |  | no | no | no | no | no | yes | yes | no | yes | no |

As can be seen from Table 3 (evaluation of shaping characteristics of Examples 1-5 and Comparative Examples 1-5), Comparative Examples 2, 3 and 5 cause a surface The above results demonstrate the importance of the constitution and compositional ratio according to the present disclosure.

INDUSTRIAL APPLICABILITY

As can be seen from the foregoing, the tablet-form cosmetic composition obtained through direct tablet pressing without using a shaping pan according to the present disclosure provides significantly improved aesthetic beauty and portability, while maintaining the cosmetic effect of the conventional powder- or cake-type powder cosmetic composition. In addition, the tablet-form cosmetic composition according to the present disclosure is shaped through granulation to solve the problem of air-filling in the tablets upon the tablet pressing. Further, it is possible to provide particles with a larger diameter and various designs.

What is claimed is:

1. A method for preparing a tablet-form makeup cosmetic composition, which comprises the steps of:
   (a) mixing makeup powder selected from the group consisting talc, mica, synthetic mica, sericite, silica, titanium dioxide, silicon powder, boron powder, zinc oxide, nylon powder, polymethacrylate powder, urethane powder, acrylate (co)polymer, polyethylene (co) polymer, organic pigments, inorganic pigments and nacreous pigments with a viscosity modifier to provide a powder blend;
   (b) spraying an aqueous dispersion containing water, an alcohol, a polymer for lubricant and a polysaccharide for binder to the powder blend while using a granulation device, wherein a granular cosmetic composition is formed
   (c) drying the granular cosmetic composition; and
   (d) carrying out direct tablet pressing of the dried granular cosmetic composition without using a shaping pan to obtain a tablet-form makeup cosmetic composition;
   wherein the tablet-form is a solid formulation having a size of 5 mm or more.

2. The method for preparing a tablet-form makeup cosmetic composition according to claim 1, wherein the viscosity modifier in (a) is a water soluble powdery viscosity modifier comprising at least one water soluble thickening agent and/or at least one gelling agent,
   wherein the water soluble thickening agent is selected from the group consisting of carrageenan, agar, gellan gum, xanthan, cellulose gum and starch, and
   wherein the inorganic gelling agent is selected from the group consisting of montmorillonite, hectorite, silicate, kaolin and zeolite.

3. The method for preparing a tablet-form makeup cosmetic composition according to claim 1, wherein the powder blend in (a) optionally further comprises at least one oil phase selected from the group consisting of silicone oil, hydrocarbon oil, wax, natural oil, and animal/vegetable liquid oil and fat.

4. The method for preparing a tablet-form makeup cosmetic composition according to claim 1, wherein the polymer for lubricant in (b) is a polymer functioning as a lubricant and selected from the group consisting of glycerin, sorbitol, mannitol, xylitol, glycols and polyhydric alcohols.

5. The method for preparing a tablet-form makeup cosmetic composition according to claim 1, wherein the polysaccharide for binder in (b) is a polysaccharide functioning as a binder and selected from the group consisting of cellulose, trehalose and glucose.

6. The method for preparing a tablet-form makeup cosmetic composition according to claim 1, the powder blend in (a) has a content of 65-90 wt % in regards to the composition and the aqueous dispersion in (b) has a content of 10-35 wt % in regards to the composition.

7. The method for preparing a tablet-form makeup cosmetic composition according to claim 1, wherein water and alcohol in (b) have a content of 15-25 wt % in regards to the composition.

* * * * *